(12) United States Patent
Balkan et al.

(10) Patent No.: US 8,143,217 B2
(45) Date of Patent: Mar. 27, 2012

(54) USE OF DPP-IV INHIBITOR TO REDUCE HYPOGLYCEMIC EVENTS

(75) Inventors: Boerk Balkan, Madison, CT (US);
David G Holmes, Binningen (CH);
Thomas E Hughes, Concord, MA (US);
Edwin B Villhauer, Morristown, NJ (US)

(73) Assignee: Novartis AG, Basel (CH)

( * ) Notice: Subject to any disclaimer, the term of this patent is extended or adjusted under 35 U.S.C. 154(b) by 673 days.

(21) Appl. No.: 12/067,314

(22) PCT Filed: Sep. 18, 2006

(86) PCT No.: PCT/US2006/036338
§ 371 (c)(1),
(2), (4) Date: Mar. 19, 2008

(87) PCT Pub. No.: WO2007/035665
PCT Pub. Date: Mar. 29, 2007

(65) Prior Publication Data
US 2008/0300171 A1      Dec. 4, 2008

Related U.S. Application Data

(60) Provisional application No. 60/718,856, filed on Sep. 20, 2005, provisional application No. 60/786,755, filed on Mar. 28, 2006.

(51) Int. Cl.
*A61K 38/28* (2006.01)
(52) U.S. Cl. ........................................................ 514/6.9
(58) Field of Classification Search ........................ None
See application file for complete search history.

(56) References Cited

U.S. PATENT DOCUMENTS

2003/0139434 A1* 7/2003 Balkan et al. ................. 514/275
2003/0225102 A1  12/2003 Sankaranarayanan ... 514/254.01

FOREIGN PATENT DOCUMENTS

| WO | WO 03/057200   | 7/2003  |
| WO | WO 2006/047248 | 5/2006  |
| WO | WO 2006/115289 | 11/2006 |

OTHER PUBLICATIONS

Deacon et al. "Inhibitors of dipeptidyl peptidase IV: a novel approach for the prevention and treatment of Type 2 diabetes?" Expert Opinion in Investigational Drugs, Aug. 18, 2004, 13, 1091-1102.*
Ahrén et al, "Improved Meal-Related Beta Cell Function and Insulin Sensitivity by the Dipeptidyl Peptidase IV Inhibitor Vildagliptin in Metformin-Treated Patients with Type 2 Diabetes Over 1 Year," Diabetes Care, Aug. 2005, 28, 1936-1940.*
Novartis "Efficacy and Safety of Vildagliptin in Combination With Insulin in Patients With Type 2 Diabetes" ClinicalTrials.gov identifier NCT00099931, First Received on Dec. 21, 2004.*
Ahren et al. ("Inhibition of Dipeptidyl Peptidase-4 Reduces Glycemia, Sustains Insulin Levels, and Reduces Glucagon Levels in Type 2 Diabetes," J. Clin. Endocrin. Metab., May 2004, 89, 2078-2084).*
Henderson et al. ("Hypoglycaemia in insulin-treated Type 2 diabetes: frequency, symptoms and impaired awareness," Diabet. Med., 2003, 20, 1016-1021).*
Wulffelé et al. ("Combination of Insulin and Metformin in the Treatment of Type 2 Diabetes," Diabetes Care, 2002, 25, 2133-2140).*
Ahren et al., "Improved meal-related β-cell function and insulin sensitivity by the dipeptidyl peptidase-IV inhibitor vildagliptin in metformin-treated patients with type 2 diabetes over 1 year", Diabetes Care, vol. 28, No. 8, pp. 1936-1940 (2005).
Ahren et al., "The DPP-4 inhibitor, LAF237, improves glycemic control in patients with type 2 diabetes (T2DM) inadequately treated with metformin", Internet Citation Abstract (XP002344251) (2004).
Ahrens et al., "Twelve-and 52-week efficacy of the dipeptidyl peptidase IV inhibitor LAF237 in metformin-treated patients with type 2 diabetes", Diabetes Care, vol. 27, No. 12, pp. 2874-2880 (2004).
Holst et al., "Glucagon-like peptide 1 and inhibitors of dipeptidyl peptidase IV in the treatment of type 2 diabetes mellitus", Current Opinion in Pharmacology, 4, pp. 589-596 (2004).
Moritoh et al., "Agent for increasing pancreatic insulin content useful for treating diabetes, contains combination of non-insulin secretion type hypoglycemic agent and dipeptidyl peptidase IV inhibitor as active ingredient" Database WPI Week 200622 Derwent Publications Ltd. (2006).
Takasaki et al., "Effects of combination treatment with dipeptidyl peptidase IV inhibitor and sulfonylurea on glucose levels in rats", Journal of Pharmacological Sciences, 95, pp. 291-293 (2004).
Wiedeman et al., "Dipeptidyl peptidase IV inhibitors for type 2 diabetes and metabolic syndrome" Drug Discovery Today: Therapeutic Strategies, vol. 2, No. 2, pp. 143-149 (2005).

* cited by examiner

*Primary Examiner* — Christina Bradley
(74) *Attorney, Agent, or Firm* — Ann R. Pokalsky, Esq.; Dilworth & Barrese, LLP

(57) ABSTRACT

The invention relates to a method to reduce the hypoglycemic events, especially sever hypoglycemic events resulting from insulin treatment, wherein the patient is treated with a Dipeptidyl peptidase IV inhibitor (DPP-IV inhibitor) or a pharmaceutically acceptable salt thereof.

10 Claims, No Drawings

200
USE OF DPP-IV INHIBITOR TO REDUCE HYPOGLYCEMIC EVENTS

This application claims benefit of U.S. Provisional Application No. 60/786,755, filed Mar. 28, 2006 and Provisional Application No. 60/718,856, filed Sep. 20, 2005, the contents of the above applications is incorporated herein in their entirety.

The invention relates to a method to reduce the hypoglycemic events, especially sever hypoglycemic events, resulting from treatment with antidiabetic compounds especially insulin treatment, wherein the patient is treated with a Dipeptidyl peptidase IV inhibitor (DPP-IV inhibitor) or a pharmaceutically acceptable salt thereof.

The treated patients are preferably suffering from hyperglycemia such as diabetes mellitus preferably non-insulin-dependent diabetes mellitus or Impaired Glucose Metabolism (IGM) preferably Impaired Glucose Tolerance (IGT).

Diabetes mellitus is a relatively common disorder (estimated at about 1% prevalence in the general population) which is characterized by hyperglycemia. There are three basic types of diabetes mellitus, type I or insulin-dependent diabetes mellitus (IDDM), type II or non-insulin-dependent diabetes mellitus (NIDDM), and type A insulin resistance. Patients with either type I or type II diabetes can become insensitive to the effects of exogenous insulin ("insulin resistant") through a variety of mechanisms. Type A insulin resistance results from either mutations in the insulin receptor gene or defects in post-receptor sites of action critical for glucose metabolism. Diabetes is generally controlled through administration of exogenous insulin (especially in type I diabetics), dietary control and exercise (especially in type II diabetics) or both.

Impaired Glucose Metabolism (IGM) is defined by blood glucose levels that are above the normal range but are not high enough to meet the diagnostic criteria for type 2 diabetes mellitus. The incidence of IGM varies from country to country, but usually occurs 2-3 times more frequently than overt diabetes. Until recently, individuals with IGM were felt to be pre-diabetics, but data from several epidemiologic studies argue that subjects with IGM are heterogeneous with respect to their risk of diabetes and their risk of cardiovascular morbidity and mortality. The data suggest that subjects with IGM, in particular IGT, do not always develop diabetes, but whether they are diabetic or not, they are, nonetheless, at high risk for cardiovascular morbidity and mortality. Among subjects with IGM, about 58% have Impaired Glucose Tolerance (IGT), another 29% have Impaired Fasting Glucose (IFG), and 13% have both abnormalities (IFG/IGT). IGT is characterized by elevated postprandial (post-meal) hyperglycemia while IFG has been defined by the ADA (see Table below) on the basis of fasting glycemic values.

The categories of Normal Glucose Tolerance (NGT), IGM and type 2 diabetes mellitus were defined by the ADA (American Diabetes Association) in 1997.

The fact that IGT is an independent risk factor in non-diabetics as well as diabetics justifies it as a new indication, separate from diabetes, for prevention and treatment of cardiovascular morbidity and mortality as well as cancer. Furthermore the stage between normoglycemia and type 2 diabetes mellitus, especially the glycemic stage, is becoming of major interest and there is a strong need for a method to inhibit or delay the progression to type 2 diabetes mellitus, and also the variety of cardiovascular and microvascular conditions and diseases as well as cancer that have been associated with IGM and especially IFG and/or IGT.

Type 2 diabetes is a progressive disease, and although monotherapy may initially control blood glucose in some patients, it is associated with a high secondary failure rate. This high incidence of therapeutic failure is a major contributor to the high rate of long-term hyperglycemia-associated complications in patients with type 2 diabetes. The limitations of single-agent therapy for maintaining glycemic control may be overcome, at least in some patients, and for a limited period of time by combining multiple oral drugs to achieve reductions in blood glucose that cannot be sustained during long-term therapy with single agents. Available data support the conclusion that in most patients with type 2 diabetes, oral monotherapy will fail and treatment with multiple drugs will be required.

But, because Type 2 diabetes is a progressive disease, even patients with good initial responses to combination therapy will eventually require an increase of the dosage or further treatment with insulin because the blood glucose level is very difficult to maintain stable for a long period of time.

Although combination therapy has the potential to enhance glycemic control, it is not without limitations. Many results indicate that the risk for hypoglycemia may increase with combination therapy, and the requirement for multiple medications may also reduce patient compliance. In addition, taking multiple antihyperglycemic drugs increases the potential for pharmacokinetic interactions with other medications that the patient may be taking.

The rational use of oral combination therapy can temporarily delay the need for multiple insulin injections, facilitate temporarily the maintenance of low glucose level or low glycosylated hemoglobin (HbA1c) level and help temporarily to prevent vascular complications.

The applicant has surprisingly discovered that DPP-IV inhibitors especially LAF237 can be used in combination with antidiabetic compounds especially in combination with insulin treatment, to reduce sever hypoglycemic events resulting from treatment with antidiabetic compounds especially insulin treatment. Furthermore the long term treatment with such a combination has significantly less inconvenient than other combinations e.g. Insulin in combination with a glitazone.

Insulin, is a known compound approved by the U.S. Food & Drug Administration for the therapeutic treatment of diabetes.

In the present context the term "insulin" is also intended to comprise any form of insulin or any derivative thereof such as described in the U.S. Pat. No. 6,620,780.

Human insulin has three primary amino groups: the N-terminal group of the A-chain and of the B-chain and the $\epsilon$-amino group of $LysB^{29}$ Several insulin derivatives which are substituted in one or more of these groups are known in the prior art. Thus, U.S. Pat. No. 3,528,960 (Eli Lilly) relates to N-carboxyaroyl insulins in which one, two or three primary ammo groups of the insulin molecule has a carboxyaroyl group. No specifically $N^{\epsilon B29}$-substituted insulins are disclosed.

According to GB Patent No. 1.492.997 (Nat. Res. Dev. Corp.), it has been found that insulin with a carbamyl substitution at $N^{\epsilon B29}$ has an improved profile of hypoglycemic effect.

P laid-open patent application No. 1-254699 (Kodama Co., Ltd.) discloses insulin wherein a fatty acid is bound to the amino group of $Phe^{B1}$ or to the $\epsilon$-amino group of $Lys^{B29}$ or to both of these. The stated purpose of the derivatisation is to obtain a pharmacologically acceptable, stable insulin preparation.

Insulins, which in the B30 position has an amino acid having at least five carbon atoms which cannot necessarily be coded for by a triplet of nucleotides, are described in JP laid-open patent application No. 57-067548 (Shionogi). The insulin analogues are claimed to be useful in the treatment of diabetes mellitus, particularly in patients who are insulin resistant due to generation of bovine or swine insulin antibodies.

U.S. Pat. No. 5,359,030 (Ekwuribe, Protein Delivery, Inc.) describes conjugation-stabilized polypeptide compositions for oral or parenteral administration comprising a polypeptide covalently coupled with a polymer including a linear polyalkylene moiety and a lipophilic moiety, said moieties being arranged so relative to each other that the polypeptide has an enhanced in vivo resistance to enzymatic degradation.

EP 511600 A2 relates i.e. to protein derivatives of the formula [protein][Z] n wherein [protein] represents a protein having n amino residues each derivable from an amino group by removal of one of its hydrogen atoms, in stead of amino groups, [Z] is a residue represented by the formula —CO—W—COOH wherein W is a divalent long chain hydrocarbon group which may also contain certain hetero atoms and n represents an average of the number of amide bonds between [Z] and [protein]. It is mentioned that the protein derivatives of the invention have an extremely prolonged serum half-life as compared with the proteins from which they are derived and that they exhibit no antigenicity. It is also mentioned, that insulin is one of the proteins from which derivatives according to the invention can be made, but no specific insulin derivatives are disclosed in EP 511600 nor is there any indication of a preferred [Z] or (a) preferred position(s) in which [Z] should be introduced in order to obtain useful insulin derivatives.

In the present specification, whenever the term insulin is used in a plural or a generic sense it is intended to encompass both naturally occurring insulins and insulin analogues and derivatives thereof. By "insulin derivative" as used herein is meant a polypeptide having a molecular structure similar to that of human insulin including the disulphide bridges between $Cys^{A7}$ and $Cys^{B7}$ and between $Cys^{A20}$ and $Cys^{B19}$ and an internal disulphide bridge between $Cys^{A6}$ and $Cys^{A11}$, and which have insulin activity.

Preferably, Insulin is in the form of a pharmaceutical composition which is a solution containing from about 30 nmol/ml to about 3000 nmol/ml, or 120 nmol/ml to 1200 nmol/ml about 600 nmol/ml of insulin.

Examples of Insulins are;

NovoLog® (insulin aspart [rDNA origin] injection) is a human insulin analog that is a rapid-acting, parenteral blood glucose-lowering agent. The dosage of NovoLog should be individualized and determined, based on the physician's advice, in accordance with the needs of the patient. The total daily individual insulin requirement is usually between 0.5-1.0 units/kg/day. When used in a meal-related subcutaneous injection treatment regimen, 50-70% of total insulin requirements may be provided by NovoLog and the remainder provided by an intermediate-acting or long-acting insulin.

APIDRA™ (insulin glulisine [rDNA origin]) is a human insulin analog that is a rapid-acting, parenteral blood glucose lowering agent. Insulin glulisine is produced by recombinant DNA technology utilizing a non-pathogenic laboratory strain of *Escherichia coli* (K12). Insulin glulisine differs from human insulin in that the amino acid asparagine at position B3 is replaced by lysine and the lysine in position B29 is replaced by glutamic acid. Chemically, it is $3^B$-lysine-$29^B$-glutamic acid-human insulin, has the empirical formula $C_{258}H_{384}N_{64}O_{78}S_6$ and a molecular weight of 5823. APIDRA 100 units per mL (U-100) is available in the following package size: 10 mL vials NDC 0088-2500-33 The dosage of APIDRA should be individualized and determined based on the physician's advice in accordance with the needs of the patient. APIDRA should normally be used in regimens that include a longer-acting insulin or basal insulin analog.

Humalog (insulin lispro, rDNA origin) is a human insulin analog that is a rapid-acting, parenteral blood glucose-lowering agent. Chemically, it is Lys(B28), Pro(B29) human insulin analog, created when the amino acids at positions 28 and 29 on the insulin B-chain are reversed.

LANTUS® (insulin glargine [rDNA origin] injection) is a sterile solution of insulin glargine for use as an injection. Insulin glargine is a recombinant human insulin analog that is a long-acting (up to 24-hour duration of action), parenteral blood-glucose-lowering agent. (See CLINICAL PHARMACOLOGY). LANTUS is produced by recombinant DNA technology utilizing a non-pathogenic laboratory strain of *Escherichia coli* (K12) as the production organism. Insulin glargine differs from human insulin in that the amino acid asparagine at position A21 is replaced by glycine and two arginines are added to the C-terminus of the B-chain. In a clinical study with insulin naïve patients with type 2 diabetes already treated with oral antidiabetes drugs, LANTUS was started at an average dose of 10 IU once daily, and subsequently adjusted according to the patient's need to a total daily dose ranging from 2 to 100 IU.

Exubera® is an inhaled short-acting insulin preparation indicated for the treatment of type I and type 2 diabetes and developed by Pfizer (insulin human [rDNA origin]) Inhalation Powder). Exubera® is a rapid-acting, dry powder human insulin that is inhaled through the mouth into the lungs prior to eating, using the handheld Exubera® Inhaler.

The term "DPP-IV inhibitor" is intended to indicate a molecule that exhibits inhibition of the enzymatic activity of DPP-IV and functionally related enzymes, such as from 1-100% inhibition, and specially preserves the action of substrate molecules, including but not limited to glucagon-like peptide-1, gastric inhibitory polypeptide, peptide histidine methionine, substance P, neuropeptide Y, and other molecules typically containing alanine or proline residues in the second aminoterminal position. Treatment with DPP-IV inhibitors prolongs the duration of action of peptide substrates and increases levels of their intact, undegraded forms leading to a spectrum of biological activities relevant to the disclosed invention.

DPP-IV can be used in the control of glucose metabolism because its substrates include the insulinotropic hormones Glucagon like peptide-1 (GLP-1) and Gastric inhibitory peptide (GIP). GLP-1 and GIP are active only in their intact forms; removal of their two N-terminal amino acids inactivates them. In vivo administration of synthetic inhibitors of DPP-IV prevents N-terminal degradation of GLP-1 and GIP, resulting in higher plasma concentrations of these hormones, increased insulin secretion and, therefore, improved glucose tolerance. For that purpose, chemical compounds are tested for their ability to inhibit the enzyme activity of purified CD26/DPP-IV. Briefly, the activity of CD26/DPP-IV is measured in vitro by its ability to cleave the synthetic substrate Gly-Pro-p-nitroanilide (Gly-Pro-pNA). Cleavage of Gly-Pro-pNA by DPP-IV liberates the product p-nitroanilide (pNA), whose rate of appearance is directly proportional to the enzyme activity. Inhibition of the enzyme activity by specific enzyme inhibitors slows down the generation of pNA. Stronger interaction between an inhibitor and the enzyme results in a slower rate of generation of pNA. Thus, the degree of inhibition of the rate of accumulation of pNA is a direct measure of the strength of enzyme inhibition. The accumulation of pNA is measured with a spectrophotometer. The inhibition constant, Ki, for each compound is determined by incubating fixed amounts of enzyme with several different concentrations of inhibitor and substrate.

In the present context "a DPP-IV inhibitor" is also intended to comprise active metabolites and prodrugs thereof, such as active metabolites and prodrugs of DPP-IV inhibitors. A "metabolite" is an active derivative of a DPP-IV inhibitor produced when the DPP-IV inhibitor is metabolised. A "prodrug" is a compound that is either metabolised to a DPP-IV inhibitor or is metabolised to the same metabolite(s) as a DPP-IV inhibitor. In the present context the term "a DPP-IV inhibitor" is also intended to comprise pharmaceutical salts thereof.

DPP-IV inhibitors are known in the art. In the following reference is made to representatives of DPP-IV inhibitors:

DPP-IV inhibitors are in each case generically and specifically disclosed e.g. in WO 98/19998, DE19616 486 A1, WO 00/34241, WO 95/15309, WO 01/72290, WO01/52825, WO03/002553, WO 9310127, WO 99/61431, WO 9925719, WO 9938501, WO 9946272, WO 9967278 and WO 9967279.

Preferred DPP-IV inhibitors are described in the following patent applications; WO 02053548 especially compounds 1001 to 1293 and examples 1 to 124, WO 02067918 especially compounds 1000 to 1278 and 2001 to 2159, WO 02066627 especially the described examples, WO 02/068420 especially all the compounds specifically listed in the examples I to LXIII and the described corresponding analogues, even preferred compounds are 2(28), 2(88), 2(119), 2(136) described in the table reporting IC50, WO 02083128 such as in the claims 1 to 5 especially compounds described in examples 1 to 13 and the claims 6 to 10, US 2003096846 especially the specifically described compounds, WO 2004/037181 especially examples 1 to 33, WO 0168603 especially compounds of examples 1 to 109, EP1258480 especially compounds of examples 1 to 60, WO 0181337 especially examples 1 to 118, WO 02083109 especially examples 1A to 1D, WO 030003250 especially compounds of examples 1 to 166, most preferably 1 to 8, WO 03035067 especially the compounds described in the examples, WO 03/035057 especially the compounds described in the examples, US2003216450 especially examples 1 to 450, WO 99/46272 especially compounds of claims 12, 14, 15 and 17, WO 0197808 especially compounds of claim 2, WO 03002553 especially compounds of examples 1 to 33, WO 01/34594 especially the compounds described in the examples 1 to 4, WO 02051836 especially examples 1 to 712, EP1245568 especially examples 1 to 7, EP1258476 especially examples 1 to 32, US 2003087950 especially the described examples, WO 02/076450 especially examples 1 to 128, WO 03000180 especially examples 1 to 162, WO 03000181 especially examples 1 to 66, WO 03004498 especially examples 1 to 33, WO 0302942 especially examples 1 to 68, U.S. Pat. No. 6,482,844 especially the described examples, WO 0155105 especially the compounds listed in the examples 1 and 2, WO 0202560 especially examples 1 to 166, WO 03004496 especially examples 1 to 103, WO 03/024965 especially examples 1 to 54, WO 0303727 especially examples 1 to 209, WO 0368757 especially examples 1 to 88, WO 03074500 especially examples 1 to 72, examples 4.1 to 4.23, examples 5.1 to 5.10, examples 6.1 to 6.30, examples 7.1 to 7.23, examples 8.1 to 8.10, examples 9.1 to 9.30, WO 02038541 especially examples 1 to 53, WO 02062764 especially examples 1 to 293, preferably the compound of example 95 (2-{{3-(Aminomethyl)-4-butoxy-2-neopentyl-1-oxo-1,2 dihydro-6-isoquinolinyl}oxy}acetamide hydrochloride), WO 02308090 especially examples 1-1 to 1-109, examples 2-1 to 2-9, example 3, examples 4-1 to 4-19, examples 5-1 to 5-39, examples 6-1 to 6-4, examples 7-1 to 7-10, examples 8-1 to 8-8, examples 7-1 to 7-7 of page 90, examples 8-1 to 8-59 of pages 91 to 95, examples 9-1 to 9-33, examples 10-1 to 10-20, US 2003225102 especially compounds 1 to 115, compounds of examples 1 to 121, preferably compounds a) to z), aa) to az), ba) to bz), ca) to cz) and da) to dk), WO 0214271 especially examples 1 to 320, US 2003096857, U.S. application Ser. No. 09/788,173 filed Feb. 16, 2001 especially the described examples, WO99/38501 especially the described examples, WO99/46272 especially the described examples and DE1 9616 486 A1 especially val-pyr, val-thiazolidide, isoleucyl-thiazolidide, isoleucyl-pyrrolidide, and fumar salts of isoleucyl-thiazolidide and isoleucyl-pyrrolidide.

Further preferred DPP-IV inhibitors include the specific examples disclosed in U.S. Pat. Nos. 6,124,305 and 6,107,317, International Patent Applications, Publication Numbers WO 9819998, WO 95153 09 and WO 9818763; such as 1[2-[(5 cyanopyridin-2-yl)aminoethylamino]acetyl-2-cyano-(S)-pyrrolidine and (2S)-1-[(2S)-2 amino-3,3-dimethylbutanoyl]-2-pyrrolidinecarbonitrile.

In a further preferred embodiment, the DPP-IV inhibitor is a N-peptidyl-O-aroyl hydroxylamine or a pharmaceutically acceptable salt thereof. Aroyl is, for example, naphthylcarbonyl; or benzoyl which is unsubstituted or mono- or disubstituted, for example, by lower alkoxy, lower alkyl, halogen or, preferably, nitro. The peptidyl moiety comprises preferably two α-amino acids, e.g. glycine, alanine, leucine, phenylalanine, lysine or proline, of which the one attached directly to the hydroxylamine nitrogen atom is preferably proline.

In each case in particular in the compound claims and the final products of the working examples, the subject matter of the final products, the pharmaceutical preparations and the claims are hereby incorporated into the present application by reference to these publications.

WO 9819998 discloses N—(N'-substituted glycyl)-2-cyano pyrrolidines, in particular 1-[2-[5-Cyanopyridin-2-yl] amino]-ethylamino]acetyl-2-cyano-(S)-pyrrolidine.

Preferred compounds described in WO03/002553 are listed on pages 9 to 11 and are incorporated into the present application by reference.

DE19616 486 A1 discloses val-pyr, val-thiazolidide, isoleucyl-thiazolidide, isoleucyl-pyrrolidide, and fumar salts of isoleucyl-thiazolidide and isoleucyl-pyrrolidide.

WO 0034241 and U.S. Pat. No. 6,110,949 disclose N-substituted adamantyl-amino-acetyl-2-cyano pyrrolidines and W (substituted glycyl)-4-cyano pyrrolidines respectively. DPP-IV inhibitors of interest are specially those cited in claims 1 to 4.

WO 9515309 discloses amino acid 2-cyanopyrrolidine amides as inhibitors of DPP-IV and WO 9529691 discloses peptidyl derivates of diesters of alpha-aminoalkylphosphonic acids, particularly those with proline or related structures. DPP-IV inhibitors of interest are specially those cited in Table 1 to 8.

In WO 01/72290 DPP-IV inhibitors of interest are specially those cited in example 1 and claims 1, 4, and 6.

WO01/52825 specially discloses (S)-1-{2-[5-cyanopyridin-2yl)amino]ethyl-aminoacetyl)-2-cyano-pyrrolidine or (S)-1-[(3-hydroxy-1-adamantyl)amino]acetyl-2-cyano-pyrrolidine (LAF237).

WO 9310127 discloses proline boronic esters useful as DPP-IV inhibitors. DPP-IV inhibitors of interest are specially those cited in examples 1 to 19.

Published patent application WO 9925719 discloses sulphostin, a DPP-IV inhibitor prepared by culturing a *Streptomyces* microorganism.

WO 9938501 discloses N-substituted 4- to 8-membered heterocyclic rings. DPP-IV inhibitors of interest are specially those cited in claims 15 to 20.

WO 9946272 discloses phosphoric compounds as inhibitors of DPP-IV. DPP-IV inhibitors of interest are specially those cited in claims 1 to 23.

Other preferred DPP-IV inhibitors are the compounds of formula I, II or III disclosed in the patent application WO 03/057200 on page 14 to 27. Most preferred DPP-IV inhibitors are the compounds specifically described on pages 28 and 29.

Published patent applications WO 9967278 and WO 9967279 disclose DPP-IV prodrugs and inhibitors of the form A-B-C where C is either a stable or unstable inhibitor of DPP-IV.

Preferably, the N-peptidyl-O-aroyl hydroxylamine is a compound of formula VII

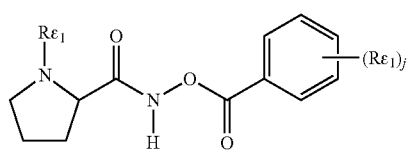

(VII)

wherein j is 0, 1 or 2;

$R\varepsilon_1$ represents the side chain of a natural amino acid; and $R\varepsilon_2$ represents lower alkoxy, lower alkyl, halogen or nitro;

or a pharmaceutically acceptable salt thereof.

In a very preferred embodiment of the invention, the N-peptidyl-O-aroyl hydroxylamine is a compound of formula VIIa

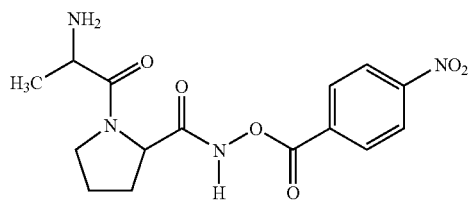

(VIIa)

or a pharmaceutically acceptable salt thereof.

N-Peptidyl-O-aroyl hydroxylamines, e.g. of formula VII or VIIa, and their preparation are described by H. U. Demuth et al. in J. Enzyme Inhibition 1988, Vol. 2, pages 129-142, especially on pages 130-132.

Preferred DPP-IV inhibitors are those described by Mona Patel and col. (Expert Opinion Investig Drugs. 2003 April; 12(4):623-33) on the paragraph 5, especially P32/98, K-364, FE-999011, BDPX, NVP-DDP-728 and others, which publication is hereby incorporated by reference especially the described DPP-IV inhibitors.

Another preferred DPP-IV inhibitor is the No. 815541 (T 6666) from Tanabe.

Preferred DPP-IV inhibitors are also described in the patent applications WO 02/083128, especially the compounds described in the examples 1 to 13, U.S. Pat. No. 6,395,767 examples 1 to 109 and WO 03/033671 all the specifically described compounds e.g. compounds 1 to 393, compounds of pages 67-70.

FE-999011 is described in the patent application WO 95/15309 page 14, as compound No. 18.

Another preferred inhibitor is the compound BMS-477118 disclosed in WO 2001068603 or U.S. Pat. No. 6,395,767 (compound of example 60) also known as is (1S,3S,5S)-2-[(2S)-2-amino-2-(3-hydroxytricyclo[3.3.1.1$^{3,7}$]dec-1-yl)-1-oxoethyl]-2-azabicyclo[3.1.0]hexane-3-carbonitrile, benzoate (1:1) as depicted in Formula M of the patent application WO 2004/052850 on page 2, and the corresponding free base, (1S,3S,5S)-2-[(2S)-2-amino-2-(3-hydroxy-tricyclo[3.3.1.1$^{3,7}$]dec-1-yl)-1-oxoethyl]-2-azabicyclo-[3.1.0]hexane-3-carbonitrile (M') and its monohydrate (M") as depicted in Formula M of the patent application WO 2004/052850 on page 3. The compound BMS-477118 is also known as saxagliptin.

Another preferred inhibitor is the compound GSK23A disclosed in WO 03/002531 (example 9) also known as (2S,4S)-1-((2R)-2-Amino-3-[(4-methoxybenzyl)sulfonyl]-3-methylbutanoyl)-4-fluoropyrrolidine-2-carbonitrile hydrochloride.

P32/98 (CAS number: 251572-86-8) also known as 3-[(2S,3S)-2-amino-3-methyl-1-oxopentyl]thiazolidine can be used as 3-[(2S,3S)-2-amino-3-methyl-1-oxopentyl]thiazolidine and (2E)-2-butenedioate (2:1) mixture and is described in WO 99/61431 and the below formula,

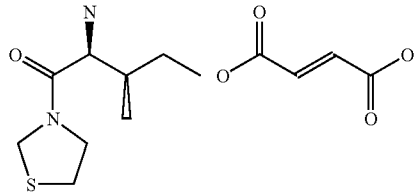

is described in WO 99/61431 and also in Diabetes 1998, 47, 1253-1258, in the name of Probiodrug, as well as the compound P93/01 described by the same company.

Other very preferred DPP-IV inhibitors are the compounds disclosed in the patent application WO 02/083128 such as in the claims 1 to 5. Most preferred DPP-IV inhibitors are the compounds specifically described by the examples 1 to 13 and the claims 6 to 10.

Other very preferred DPP-IV inhibitors are the compounds disclosed By Bristol-Myers Squibb such as Saxagliptin (BMS477118).

Other very preferred DPP-IV inhibitors of the invention are described in the International patent application WO 02/076450 (especially the examples 1 to 128) and by Wallace T. Ashton (Bioorganic & Medicinal Chemistry Letters 14 (2004) 859-863) especially the compound 1 and the compounds listed in the tables 1 and 2. The preferred compound is the compound 21e (table 1) of formula:

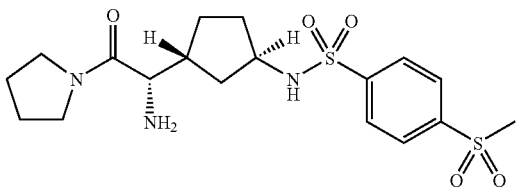

Other preferred DPP-IV inhibitors are described in the patent applications WO 2004/037169 especially those described in the examples 1 to 48 and WO 02/062764 especially the described examples 1 to 293, even preferred are the compounds 3-(aminomethyl)-2-isobuthyl-1-oxo-4-phenyl-1,2-dihydro-6-isoquinolinecarboxamide and 2-{[3-(aminomethyl)-2-isobuthyl-4-phenyl-1-oxo-1,2-dihydro-6-isoquinolyl]oxy}acetamide described on page 7 and also in the patent application WO2004/024184 especially in the reference examples 1 to 4.

Other preferred DPP-IV inhibitors are described in the patent application WO 03/004498 especially examples 1 to 33 and most preferably the compound of the formula

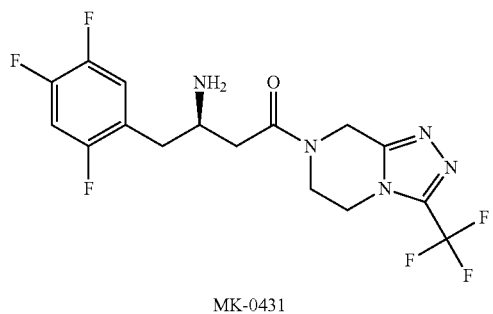

MK-0431 described by the example 7 and also known as MK-0431 or Sitagliptin. The preferred daily administration of sitagliptin is between 25 and 100 mg.

In each case in particular in the compound claims and the final products of the working examples, the subject matter of the final products, the pharmaceutical preparations and the claims are hereby incorporated into the present application by reference to these publications.

Preferred DPP-IV inhibitors are also described in the patent application WO 2004/037181 especially examples 1 to 33 and most preferably the compounds described in the claims 3 to 5.

Preferred DPP-IV inhibitors are N-substituted adamantyl-amino-acetyl-2-cyano pyrrolidines, N(substituted glycyl)-4-cyano pyrrolidines, N—(N'-substituted glycyl)-2-cyanopyrrolidines, N-aminoacyl thiazolidines, N-aminoacyl pyrrolidines, L-allo-isoleucyl thiazolidine, L-threo-isoleucyl pyrrolidine, and L-allo-isoleucyl pyrrolidine, 1-[2-[(5-cyanopyridin-2-yl)amino]ethylamino]acetyl-2-cyano-(S)-pyrrolidine, MK-431 and pharmaceutical salts thereof.

Most preferred DPP-IV inhibitors are selected from [S]-1-[2-(5-cyano-2-pyridinylamino)ethylamino]acetyl-2-pyrolidine carbonitrile monohydrochloride, (S)-1-[(3-hydroxy-1-adamantyl)amino]acetyl-2-cyano-pyrrolidine and L-threo-isoleucyl thiazolidine (compound code according to Probiodrug: P32/98 as described above), MK-0431, 3-(aminomethyl)-2-isobuthyl-1-oxo-4-phenyl-1,2-dihydro-6-isoquinolinecarboxamide and 2-{[3-(aminomethyl)-2-isobuthyl-4-phenyl-1-oxo-1,2-dihydro-6-isoquinolyl]oxy}acetamide and optionally pharmaceutical salts thereof.

[S]-1-[2-(5-cyano-2-pyridinylamino)ethylamino]acetyl-2-pyrolidine carbonitrile monohydrochloride and (S)-1-[(3-hydroxy-1-adamantyl)amino]acetyl-2-cyano-pyrrolidine are specifically disclosed in Example 3 of WO 98/19998 and Example 1 of WO 00/34241, respectively. The DPP-IV inhibitor P32/98 (see above) is specifically described in Diabetes 1998, 47, 1253-1258. [S]-1-[2-(5-cyano-2-pyridinylamino)ethylamino]acetyl-2-pyrolidine carbonitrile monohydrochloride and (S)-1-[(3-hydroxy-1-adamantyl)amino]acetyl-2-cyano-pyrrolidine can be formulated as described on page 20 of WO 98/19998 or in WO 00/34241.

Especially preferred are 1-{2-[(5-cyanopyridin-2-yl)amino]ethylamino}acetyl-2-(S)-cyano-pyrrolidine (also named [S]-1-[2-(5-cyano-2-pyridinylamino)ethylamino]acetyl-2-pyrolidine carbonitrile monohydrochloride), of formula:

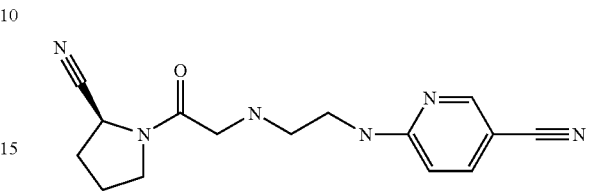

especially the dihydrochloride and monohydrochloride form thereof, pyrrolidine, 1-[(3-hydroxy-1-adamantyl)amino]acetyl-2-cyano-, (S) (also named (S)-1-[(3-hydroxy-1-adamantyl)amino]acetyl-2-cyano-pyrrolidine, LAF237 or vildagliptin) of formula

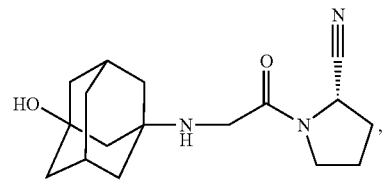

and L-threo-isoleucyl thiazolidine (compound code according to Probiodrug: P32/98 as described above), Sitagliptin, GSK23A, saxagliptin, 3-(aminomethyl)-2-isobuthyl-1-oxo-4-phenyl-1,2-dihydro-6-isoquinolinecarboxamide and 2-{[3-(aminomethyl)-2-isobuthyl-4-phenyl-1-oxo-1,2-dihydro-6-isoquinolyl]oxy}acetamide and optionally in any case pharmaceutical salts thereof.

DPP728 and LAF237 are specifically disclosed in Example 3 of WO 98/19998 and Example 1 of WO 00/34241, respectively. The DPP-IV inhibitor P32/98 (see above) is specifically described in Diabetes 1998, 47, 1253-1258. DPP728 and LAF237 can be formulated as described on page 20 of WO 98/19998 or in WO 00/34241, or in the International Patent Application No. EP2005/000400 (application number).

Any of the substances disclosed in the above mentioned patent documents or scientific publications, hereby included by reference, are considered potentially useful as DPP-IV inhibitors to be used in carrying out the present invention.

DPP-IV inhibitor to be used alone according to the present invention can be used in association with a carrier.

A carrier in the instant context is a tool (natural, synthetic, peptidic, non-peptidic) for example a protein which transports specific substances through the cell membrane in which it is embedded and into the cell. Different carriers (natural, synthetic, peptidic, non-peptidic) are required to transport different substances, as each one is designed to recognize only one substance, or group of similar substances.

Any means of detection known by the person skilled in the art can be used to detect the association of the DPP-IV with a carrier, for example, by labelling the carrier.

The DPP-IV inhibitor can be a peptidic or, preferably, non-peptidic one.

Most preferred are orally active DPP-IV inhibitors and pharmaceutical salts thereof.

The active ingredients (DPP-IV inhibitors) or pharmaceutically acceptable salts thereof according to the present invention may also be used in form of a solvate, such as a hydrate or including other solvents, used for crystallization.

It has now been surprisingly found that DPP-IV inhibitors or a salt thereof, especially LAF237 can be used in combination with at least one antidiabetic compound (e.g. one or two antidiabetic compounds) especially Insulin to reduce the sever hypoglycemic events resulting from treatment with the antidiabetic compound especially to reduce the sever hypoglycemic events resulting from insulin treatment. Thus in a first embodiment, this invention provides a method for reducing the sever hypoglycemic events comprising administering a therapeutically effective amount of DPP-IV inhibitor or a salt thereof, to a patient treated by at least one antidiabetic compound (e.g. one or two antidiabetic compounds) especially to a patient treated by insulin.

Or a method for reducing the hypoglycemic events or sever hypoglycemic events resulting from treatment with at least one antidiabetic compound (i.e. one or two antidiabetic compounds) especial resulting from insulin treatment, comprising administering a therapeutically effective amount of DPP-IV inhibitor or a salt thereof, to a patient treated by antidiabetics especially to a patient treated by insulin.

Or the use of a DPP-IV inhibitor or a salt thereof, in combination with at least one antidiabetic compound (e.g. one or two antidiabetic compounds) especially insulin for the manufacture of a medicament for the reduction of the hypoglycemic events or sever hypoglycemic events.

Or the use of a DPP-IV inhibitor or a salt thereof, for the manufacture of a medicament for the reduction of hypoglycemic events or sever hypoglycemic events, in patients treated by at least one antidiabetic compound (e.g. one or two antidiabetic compounds) especially in patients under insulin treatment.

Use as herein described, wherein the hypoglycemic events or sever hypoglycemic events are resulting from insulin treatment i.e. consequential to insulin treatment.

Use as herein described, wherein the hypoglycemic events or sever hypoglycemic events are resulting from treatment i.e. consequential to treatment, with antidiabetic compounds e.g. with one, two or three, selected from metformin, nateglinide, glitazones (preferably pioglitazone or rosiglitazone), sulfonylureas, GLP-1 or GLP-1 analogues (preferably exendin-4), a cannabinoid receptor-1 (CB1) antagonists (preferably rimonaban) and insulin. When the patient is treated with two antidiabetic compounds, the combination can be; metformin+a sulfonylureas, metformin+a glitazone, metformin+a GLP-1 analogue, metformin+a CB1 antagonist, a glitazone+a sulfonylurea, metformin+insulin, a glitazone+ insulin, a GLP-1 analogue+a sulfonylurea, a sulfonylurea+ insulin, or a GLP-1 analogue+insulin.

The terms "hypoglycemic event" or "hypoglycemic episode" are well known by the person skilled in the art. Hypoglycemia was defined as symptoms suggestive of low blood glucose confirmed by SMBG<3.1 mmol/L plasma glucose equivalent. Severe hypoglycemia was defined as any episode requiring the assistance of another party (with low plasma glucose value<3.1 mmol/L unless the severity of the event precluded glucose determination). Therefore according to the present invention, the term "Severe hypoglycemia" is preferably defined as an episode of low plasma glucose value<3.8 mmol/L, preferably<3.1 mmol/L.

Preferably the DPP-IV inhibitor is (S)-1-[(3-hydroxy-1-adamantyl)amino]acetyl-2-cyano-pyrrolidine (LAF237 or vildagliptin) of formula (I)

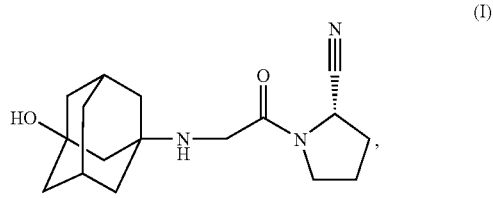

or pharmaceutically acceptable salt thereof.

In the present context the terms "(S)-1-[(3-hydroxy-1-adamantyl)amino]acetyl-2-cyano-pyrrolidine" or "LAF237" or "vildagliptin" is also intended to comprise any salt or crystal form thereof.

Antidiabetic compounds are preferably selected from the group consisting of insulin signalling pathway modulators, like inhibitors of protein tyrosine phosphatases (PTPases), non-small molecule mimetic compounds and inhibitors of glutamine-fructose-6-phosphate amidotransferase (GFAT), compounds influencing a dysregulated hepatic glucose production, like inhibitors of glucose-6-phosphatase (G6Pase), inhibitors of fructose-1,6-bisphosphatase (F-1,6-BPase), inhibitors of glycogen phosphorylase (GP), glucagon receptor antagonists and inhibitors of phosphoenolpyruvate carboxykinase (PEPCK), pyruvate dehydrogenase kinase (PDHK) inhibitors, insulin sensitivity enhancers, insulin secretion enhancers, α-glucosidase inhibitors, inhibitors of gastric emptying, insulin, and $α_2$-adrenergic antagonists, or CB1 cannabinoid receptor antagonists.

The term "insulin sensitivity enhancer" used herein means any and all pharmacological active compounds that enhance the tissue sensitivity towards insulin. Insulin sensitivity enhancers include, e.g., inhibitors of GSK-3, retinoid X receptor (RXR) agonists, agonists of Beta-3 AR, agonists of UCPs, antidiabetic thiazolidinediones (glitazones), non-glitazone type PPARγ agonists, dual PPARγ/PPARα agonists, antidiabetic vanadium containing compounds and biguanides, e.g., metformin.

The insulin sensitivity enhancer is preferably selected from the group consisting of antidiabetic thiazolidinediones, antidiabetic vanadium containing compounds and metformin.

In one preferred embodiment, the insulin sensitivity enhancer is metformin.

Metformin has been widely prescribed for lowering blood glucose in patients with NIDDM and is marketed in 500, 750, 850 and 1000 mg strengths. However, because it is a short acting drug, metformin requires twice-daily or three-times-daily dosing (500-850 mg tab 2-3/day or 1000 mg bid with meals). The biguanide antihyperglycemic agent metformin disclosed in U.S. Pat. No. 3,174,901 is currently marketed in the U.S. in the form of its hydrochloride salt (Glucophage@), Bristol-Myers Squibb Company). The preparation of metformin (dimethyidiguanide) and its hydrochloride salt is state of the art and was disclosed first by Emil A. Werner and James Bell, J. Chem. Soc. 121, 1922, 1790-1794. Metformin, can be administered e.g. in the form as marketed under the trademarks GLUCOPHAGE™.

Mefformin, increases the sensitivity to insulin in peripheral tissues of the hosts. Mefformin is also involved in inhibition of glucose absorption from the intestine, suppression of hepatic gluconeogenesis, and inhibition of fatty acid oxidation. Suitable dosage regimens of Metformin include unit doses of 500 mg two to three time's daily and can even be build up to five times daily or 850 mg once or twice daily. [Martindale, The Complete Drug Reference.

Certain controlled or sustained release formulations that employ antihyperglycemic drugs such as metformin hydrochloride have been limited to the use of an expanding or gelling agent to control the release of the drug from the dosage form. This research is exemplified by the teachings of WO 96/08243 and by the GLUCOPHAGE XR product insert which is a controlled release metformin product commercially available from Bristol-Myers Squibb. GLUCOPHAGE (metformin hydrochloride tablets) should be given in divided doses with meals while GLUCOPHAGE XR (metformin hydrochloride extended-release tablets) should generally be given once daily With the evening meal. Metformin is preferably in the form of metformin HCl.

The term "metformin" as employed herein refers to metformin or a pharmaceutically acceptable salt thereof such as the hydrochloride salt, the metformin (2:1) fumarate salt, and the metformin (2:1) succinate salt as disclosed in U.S. application Ser. No. 09/262,526 filed Mar. 4, 1999, the hydrobromide salt, the p-chlorophenoxy acetate or the embonate, and other known metformin salts of mono and dibasic carboxylic acids including those disclosed in U.S. Pat. No. 3,174,901, all of which salts are collectively referred to as metformin. It is preferred that the metformin employed herein be the metformin hydrochloride salt, namely, that marketed as GLUCOPHAGE-D or GLUCOPHAGE XR (trademark of Bristol-Myers Squibb Company).

In the present context "a DPP-IV inhibitor", "metformin", "a glitazone", or any specific glitazone like "pioglitazone", "rosiglitazone", is also intended to comprise any pharmaceutically acceptable salt thereof, crystal form, hydrate, solvate, diastereoisomer or enantiomer thereof.

The antidiabetic thiazolidinedione (glitazone) is, for example, (S)-((3,4-dihydro-2-(phenylmethyl)-2H-1-benzopyran-6-yl)methyl-thiazolidine-2,4-drone (englitazone), 5-{[4-(3-(5-methyl-2-phenyl-4-oxazolyl)-1-oxopropyl)-phenyl]-methyl}-thiazolidine-2,4-dione (darglitazone), 5-{[4-(1-methyl-cyclohexyl)methoxy)-phenyl]methyl}-thiazolidine-2,4-dione (ciglitazone), 5-{[4-(2-(1-indolyl)ethoxy) phenyl]methyl}-thiazolidine-2,4-dione (DRF2189), 5-{4-[2-(5-methyl-2-phenyl-4-oxazolyl)-ethoxy)]benzyl}-thiazolidine-2,4-dione (BM-13.1246), 5-(2-naphthylsulfonyl)-thiazolidine-2,4-dione (AY-31637), bis{4-[(2,4-dioxo-5-thiazolidinyl)-methyl]phenyl}methane (YM268), 5-{4-[2-(5-methyl-2-phenyl-4-oxazolyl)-2-hydroxyethoxy]-benzyl}-thiazolidine-2,4-dione (AD-5075), 5-[4-(1-phenyl-1-cyclopropanecarbonylamino)-benzyl]-thiazolidine-2,4-dione (DN-108) 5-{[4-(2-(2,3-dihydroindol-1-yl)ethoxy)phenylmethyl}-thiazolidine-2,4-dione, 5-[3-(4-chloro-phenyl])-2-propynyl]-5-phenylsulfonyl)thiazolidine-2,4-dione, 5-[3-(4-chlorophenyl])-2-propynyl]-5-(4-fluorophenyl-sulfonyl)thiazolidine-2,4-dione, 5-{[4-(2-(methyl-2-pyridinyl-amino)-ethoxy)phenyl]methyl}-thiazolidine-2,4-dione (rosiglitazone), 5-{[4-(2-(5-ethyl-2-pyridyl)ethoxy)phenyl]-methyl}thiazolidine-2,4-dione (pioglitazone), 5-{[4-((3,4-dihydro-6-hydroxy-2,5,7,8-tetramethyl-2H-1-benzopyran-2-yl)methoxy)-phenyl]-methyl}-thiazolidine-2,4-dione (troglitazone), 5-[6-(2-fluorobenzyloxy)naphthalen-2-ylmethyl]-thiazolidine-2,4-dione (MCC555), 5-{[2-(2-naphthyl)-benzoxazol-5-yl]-methyl}thiazolidine-2,4-dione (T-174) and 5-(2,4-dioxothiazolidin-5-ylmethyl)-2-methoxy-N-(4-trifluoromethyl-benzyl)benzamide (KRP297).

Specific glitazone like "pioglitazone", "rosiglitazone", is also intended to comprise any pharmaceutically acceptable salt thereof, crystal form, hydrate, solvate, diastereoisomer or enantiomer thereof.

For administration of a PPAR ANTIDIABETIC especially a glitazone to an adult diabetic patient (body weight: 50 kg), for instance, the dose per day is usually 0.01 to 1000 mg, preferably 0.1 to 500 mg. This dose can be administered once to several times a day.

Especially, when pioglitazone hydrochloride is employed as the insulin sensitizer, the dose of pioglitazone hydrochloride per day is usually 7.5 to 60 mg, preferably 15 to 45 mg. When troglitazone is employed as the insulin sensitizer, the dose of troglitazone per day is usually 100 to 1000 mg, preferably 200 to 600 mg. When rosiglitazone (or its maleate) is employed as the insulin sensitizer, the dose of rosiglitazone per day is usually 1 to 12 mg, preferably 2 to 12 mg.

The glitazone is preferably pioglitazone, pioglitazone hydrochloride, troglitazone or rosiglitazone (or its maleate salt), especially preferably pioglitazone hydrochloride.

The dose of ACTOS® (pioglitazone) should not exceed 45 mg once daily in monotherapy or in combination with sulfonylurea, metformin, or insulin. ACTOS in combination With metformin may be initiated at 15 mg or 30 mg once daily. The current metformin dose can be continued upon initiation of ACTOS therapy. It is unlikely that the dose of metformin will require adjustment due to hypoglycemia during combination therapy with ACTOS. ACTOS is available in 15 mg, 30 mg, and 45 mg tablets AVANDIA® (rosiglitazone) may be administered either at a starting dose of 4 mg as a single daily dose or divided and administered in the morning and evening. For patients who respond inadequately following 8 to 12 weeks of treatment, as determined by reduction in FPG, the dose may be increased to 8 mg daily as monotherapy or in combination with metformin. The dose of AVANDIA should not exceed 8 mg daily, as a single dose or divided twice daily. AVANDIA is available in 2 mg, 4 mg, and 8 mg tablets Marketed combinations comprising metformin and a thiazolidinedione derivative can also be used according to the present invention. In particular it can be possible to administer rosiglitazone in combination with metformin in the form as it is marketed e.g. under the trademark AVANDAMET®. The dosage of antidiabetic therapy with AVANDAMET should be individualized on the basis of effectiveness and tolerability while not exceeding the maximum recommended daily dose of 8 mg/2,000 mg. AVANDAMET® provides different kind of tablets. Each tablet contains rosiglitazone as the maleate and metformin hydrochloride as follows: 1 mg/500 mg, 2 mg/500 mg, 4 mg/500 mg, 2 mg/1,000 mg, 4 mg/1,000 mg.

Non-glitazone type PPARγ agonists are especially N-(2-benzoylphenyl)-L-tyrosine analogues, e.g. GI-262570, and JTT501.

Insulin secretion enhancers are pharmacological active compounds having the property to promote secretion of insulin from pancreatic β cells. Examples for insulin secretion enhancers include glucagon receptor antagonists (see above), sulphonyl urea derivatives, incretin hormones, especially glucagon-like peptide-1 (GLP-1) or GLP-1 agonists, β-cell imidazoline receptor antagonists, and short-acting insulin secretagogues, like antidiabetic phenylacetic acid derivatives, antidiabetic D-phenylalanine derivatives and BTS 67582 described by T. Page et al in Br. J. Pharmacol. 1997, 122, 1464-1468.

The sulphonyl urea derivative is, for example, glisoxepid, glyburide, glibenclamide, acetohexamide, chlorpropamide, glibornuride, tolbutamide, tolazamide, glipizide, carbutamide, gliquidone, glyhexamide, phenbutamide or tolcyclamide; and preferably glimepiride or gliclazide. Tolbutamide, glibenclamide, gliclazide, glibornuride, gliquidone, glisoxepid and glimepiride can be administered e.g. in the form as they are marketed under the trademarks RASTINON HOECHST™, AZUGLUCON™, DIAMICRON™, GLUBORID™, GLURENORM™, PRO-DIABAN™ and AMARYL™, respectively.

GLP-1 is a insulinotropic proteine which was described, e.g., by W. E. Schmidt et al. in Diabetologia 28, 1985, 704-707 and in U.S. Pat. No. 5,705,483. The term "GLP-1 agonists" used herein means variants and analogs of GLP-1(7-36)NH$_2$ which are disclosed in particular in U.S. Pat. No. 5,120,712, U.S. Pat. No. 5,118,666, U.S. Pat. No. 5,512,549, WO 91/11457 and by C. Orskov et al in J. Biol. Chem. 264 (1989) 12826. The term "GLP-1 agonists" comprises especially compounds like GLP-1 (7-37), in which compound the carboxy-terminal amide functionality of Arg$^{36}$ is displaced with Gly at the 37$^{th}$ position of the GLP-1 (7-36)NH$_2$ molecule and variants and analogs thereof including GLN$^9$-GLP-1(7-37), D-GLN$^9$-GLP-1(7-37), acetyl LYS$^9$-GLP-1(7-37), LYS$^{18}$-GLP-1(7-37) and, in particular, GLP-1(7-37)OH, VAL8-GLP-1(7-37), GLY$^8$-GLP-1(7-37), THR$^8$-GLP-1(7-37), MET$^8$-GLP-1(7-37) and 4-imidazopropionyl-GLP-1. Special preference is also given to the GLP agonist analog exendin-4, described by Greig et al in Diabetologia 1999, 42, 45-50. BYETTA (exendin-4) is the first in a new class of drugs for the treatment of type 2 diabetes called incretin mimetics and exhibits many of the same effects as the human incretin hormone glucagon-like peptide-1 (GLP-1) and is claimed in the U.S. Pat. No. 5,424,286. BYETTA is formulated for self-administration as a fixed dose, subcutaneous injection given prior to the morning and evening meals. BYETTA will be made available in both a 5-microgram per dose and a 10-microgram per dose prefilled pen-injector device.

An antagonist of the CB1 cannabinoid receptor is a compound which binds to the receptor and lacks any substantial ability to activate the receptor itself. An antagonist can thereby prevent or reduce the functional activation or occupation of the receptor by an agonist such as anandamide when the agonist is present. In some embodiments, the antagonist has an IC$_{50}$ from about 1 µM to about 1 nM. In other embodiments, the antagonist has an IC$_{50}$ of from about 0.1 µM to 0.01 µM, 1.0 µM to 0.1 µM, or 0.01 µM to 1 nM. In some embodiments, the antagonist competes with the agonist for binding to a shared binding site on the receptor.

A first group of suitable cannabinoid CB1 receptor antagonists are pyrazole derivatives. Patent applications EP-A-576 357 and EP-A-658 546 describe exemplary pyrazole derivatives which have an affinity for the cannabinoid receptors. More particularly, patent application EP-A-656 354 discloses exemplary pyrazole derivatives and claims N-piperidino-5-(4-chlorophenyl)-1-(2,4-dichlorophenyl)-4-methylpyrazole-3-carboxamide, or SR 141716, and its pharmaceutically acceptable salts, which have a very good affinity for the central cannabinoid receptors. Additional exemplary CB1 receptor antagonists are disclosed in U.S. Pat. No. 5,596,106 which discloses both arylbenzo[b]thiophene and benzo[b]furan compounds to block or inhibit cannabinoid receptors in mammals. Preferably, such a cannabinoid antagonist is selective for the CB1 receptor and has an IC$_{50}$ for the CB1 receptor which is one-fourth or less than that of the CB2 receptor or, more preferably, is one-tenth or less than the IC$_{50}$ for the CB2 receptor, or even more preferably, an IC$_{50}$ with respect to the CB1 receptor which is one-hundredth that for the CB2 receptor. Each of the above references is incorporated by reference in its entirety.

Other examples of selective CB$_1$ antagonistic compounds which are useful in the context of the present invention include (without being limited thereto):

1) Diarylpyrazole congeners disclosed by Sanofi as selective CB, receptor antagonists, e.g. as representative example the compounds SR-141716A, SR-147778, SR-140098 and rimonabant and related compounds described e.g. in EP 0969835 or EP 1150961 (Central mediation of the cannabinoid cue: activity of a selective CB$_1$ antagonist, SR 141716A Perio A, Rinaldi-Carmona M, Maruani J Behavioural Pharmacology 1996, 7:1 (65-71)); WIN-54461 disclosed by Sanofi-Winthrop (Cannabinoid receptor ligands: Clinical and neuropharmacological considerations relevant to future drug discovery and development. Pertwee R G, Expert Opinion on Investigational Drugs 1996, 5:10 (1245-1253)). N-piperidino-5-(4-chlorophenyl)-1-(2,4-dichlorophenyl)-4-methylpyrazole-3-carboxamide (SR 141616-CAS number: 168273-06-1), its pharmaceutically acceptable salts and their solvates were described for the preparation of drugs useful in the treatment of appetency disorders. SR 141616, (pINN: rimonabant) is represented by the formula:

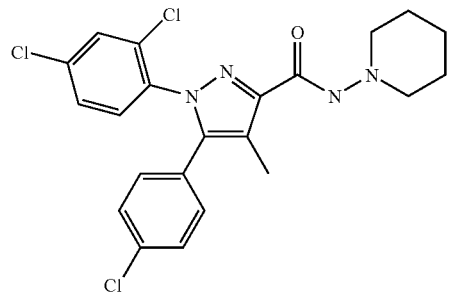

Rimonabant is specifically described in EP-B-656 354 or in an article from M. Rinaldi-Carmona et al. (FEBS Lett., 1994, 350, 240-244). EP1446384 A1 describes new polymorphs of rimonabant, formulation comprising rimonabant are described in WO2003082256, and the use of rimonabant in apetite disorders is described in WO99/00119.

2) Aminoalkylindoles having been disclosed as CB$_1$ receptor antagonists, e.g. as a representative example the compound lodopravadoline (AM-630), 3) Aryl-aroyl substituted benzofurans described by Eli Lilly as selective CB$_1$ receptor antagonists, e.g. LY-320135 (Cannabinoid receptor ligands: Clinical and neuropharmacological considerations relevant to future drug discovery and development. Pertwee R G, Expert Opinion on Investigational Drugs 1996, 5:10 (1245-1253)), 4) Compounds described by Merck & Co, e.g. AM 251 and AM 281 (Conference: 31st Annual Meeting of the Society for Neuroscience, San Diego, USA, 10-15 Nov. 2001), and substituted imidazolyl derivatives disclosed e.g. in U.S. 2003-114495 or WO 03/007887, 5) Azetidine derivatives described by Aventis Pharma e.g. in WO 02/28346 or EP 1328269, 6) CP-55940 from Pfizer Inc. (Comparison of the pharmacology and signal transduction of the human cannabinoid CB1 and CB2 receptors, Felder C C, Joyce K E, Briley E M, Mansouri J, Mackie K, Blond O, Lai Y, Ma A L, Mitchell R L, Molecular Pharmacology 1995, 48:3 (443)), 6') The Pfizer compounds described in the patent applications EP1622876, EP1622902, EP1622903, EP162290, EP1622909, EP1638570, EP1594872, EP1592691, EP1558615, EP1556373, EP1572662 especially the specific examples described therein, especially CP-945598.

7) Diaryl-pyrazine-amide derivatives from Astra Zeneca described e.g. in the WO 03/051851, 8) ACPA and ACEA from Med. Coll. Wisconsin (Univ. Aberdeen), ("Effects of AM 251 & AM 281, cannabinoid CB1 antagonists, on palatable food intake in lewis rats" J. Pharmacol. Exp. Ther. 289, No 3, 1427-33, 1999), 9) Pyrazole derivatives described by the University of Connecticut e.g. in the WO 01/29007, 10) HU-210 (International Association for the Study of Pain—Ninth World Congress (Part II) Vienna, Austria, Dickenson A H, Carpenter K, Suzuki R, IDDB MEETING REPORT 1999, Aug. 22-27) and HU-243 (Cannabinoid receptor agonists and antagonists, Barth F, Current Opinion in Therapeutic Patents 1998, 8:3 (301-313)) from Yissum R&D Co Hebrew Univ. of Jerusalem, 11) O-823 from Organix Inc. (Drug development pipeline: O-585, O-823, O-689, O-1072, nonamines, Orgaix, Altropane Organix Inc, Company Communication 1999, Aug. 10; IDDb database) and O-2093 from Consiglio Nazionale delle Ricerche ("A structure/activity relationship study on arvanil, endocannabinoid and vanilloid hybrid.", Marzo D V, Griffin G, Petrocellis L, Brandi I, Bisogno T, Journal of Pharmacology and Experimental Therapeutics 2002, 300:3 (984-991)), 12) 3-Alkyl-5,5'-diphenylimidazolidinediones which were described as cannabinoid receptor ligands, 13) $CB_1$ antagonistic compounds currently under development by Bayer AG (IDDb database: company communication 2002, Feb. 28).

14) CB1 receptor antagonists are pyrazole derivatives according to Formula (I) Of U.S. Pat. No. 6,028,084 which is incorporated by reference in its entirety.

15) U.S. Pat. No. 6,017,919 discloses another group of suitable cannabinoid receptor antagonists for use according to the invention. These antagonists are of the following general formula:

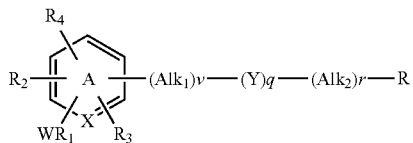

wherein the substituents are as defined in U.S. Pat. No. 6,017,919 which is incorporated herein by reference in its entirety.

16) The CB1 cannabinoid antagonist is a 4,5, dihydro-1H-pyrazole derivative having CB1-antagonist activity as taught in U.S. Pat. No. 5,747,524 and U.S. Patent Application No. 2001/0053788A1 published on Dec. 20, 2001.

17) The CB1 receptor antagonist is a 4,5,dihydro-1H-pyrazole derivative having CB1-antagonistic activity as taught in U.S. Patent Application No. 2001/0053788A1 and particularly disclosed by formula (I) therein. U.S. Patent Application No. 2001/0053788A1 published on Dec. 20, 2001 and is incorporated by reference in its entirety.

18) The CB1 receptor antagonists described in WO2005049615 especially the compounds of example 1 to 8.

19) The CB1 receptor antagonists described in WO2005047285 especially the compounds of example 1 to 99.

20) The CB1 receptor antagonist (4R)-3-(4-chlorophenyl)-4,5-dihydro-N-methyl-4-phenyl-N'-[[4-(trifluoromethyl)phenyl]sulfonyl]-1H-pyrazole-1-carboximidamide (SLV 326-34th Neuroscience, Abs 1009.4, October 2004)

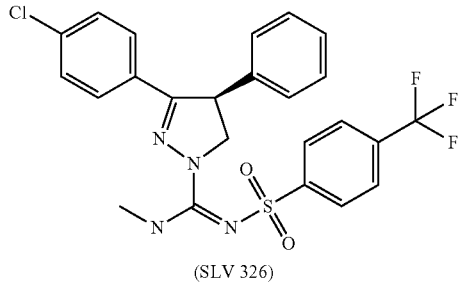

(SLV 326)

developed by the company Solvay (WO0170700 A1).

Solvay CB1 receptor antagonists are described in the examples of the patent applications WO2005040130 A1, WO2005028456 A1, WO2005020988 A1, WO2004026301 A1, WO2003078413 A1, WO2003027076 A2, WO2003026648 A1, WO2003026647 A1, WO2002076949 A1, WO0170700 A1.

Daily rimonabant dosages required in practicing the method of the present invention will vary depending upon, for example the mode of administration and the severity of the condition to be treated. An indicated daily dose is in the range of from about 1 to about 100 mg, e.g. from 5 to 50 mg or from 5 to 20 mg, of active agent for oral use, conveniently administered once or in divided dosages.

Preferably the treated patient according to the invention is suffering from hyperglycemia.

Most preferably the patient is suffering from a disease selected from diabetes mellitus, type I or insulin-dependent diabetes mellitus (IDDM), type II or non-insulin-dependent diabetes mellitus (NIDDM), type A insulin resistance, Impaired Glucose Metabolism (IGM), Impaired Fasting Glucose (IFG) or Impaired Glucose Tolerance (IGT). In a preferred embodiment the patient is suffering from type II diabetes or IGT.

In a most preferred embodiment the DPP-IV inhibitor or a salt thereof, is added to the standard diabetes treatment in patients whose disease i.e. diabetes, was not adequately controlled by insulin alone or by the treatment with one, two or three antidiabetic compounds. The criteria's to evaluate the proper disease control are well known by the person skilled in the art and described in literature e.g. every year by American Diabetes Association in the review Diabetes Care (Standards of Medical Care in Diabetes 2006-29: S4-42S).

The present methods or uses are particularly useful for the prevention or delay of progression of conditions associated with type II diabetes or IGT, particularly cardiovascular and microvascular conditions.

The invention furthermore relates to the use of a DPP-IV inhibitor or a salt thereof, for the manufacture of a medicament to reduce the hypoglycemic events or sever hypoglycemic events, in patients treated with at least one antidiabetic compound (e.g. one or two antidiabetic compounds) or in insulin treated patient, particularly in a patient (e.g. type II diabetic patient) not adequately controlled by the treatment with at least one antidiabetic compound (e.g. one or two antidiabetic compounds) or by insulin alone i.e. diabetes or glucose level not adequately controlled by at least one antidiabetic compound or insulin alone.

Preferably the invention relates to the use of a DPP-IV inhibitor or a salt thereof, in combination with at least one antidiabetic compound (one, two or three antidiabetic compounds) or insulin, for the manufacture of a medicament to reduce the hypoglycemic events or sever hypoglycemic events in a patient (e.g. type II diabetic patient) not adequately controlled by the one or more antidiabetic compounds or insulin alone i.e. diabetes or glucose level not adequately controlled by at least one antidiabetic compound (one, two or three antidiabetic compounds) or insulin alone.

Method or use as herein described, wherein between 25 and 150 mg, preferably 50 mg or 100 mg of vildagliptin, or a salt thereof, is to be administered, preferably daily (daily dose).

Furthermore as used herein, "a daily dose" means the dose given within a 24-hour period.

The term "prevention" means prophylactic administration of the combination to healthy patients to prevent the outbreak of the conditions mentioned herein. Moreover, the term "prevention" means prophylactic administration of such combination to patients being in a pre-stage of the conditions, to be treated.

The term "delay of progression" used herein means administration of the combination, such as a combined preparation or pharmaceutical composition, to patients being in a pre-stage of the condition to be treated in which patients a pre-form of the corresponding condition is diagnosed.

By the term "treatment" is understood the management and care of a patient for the purpose of combating the disease, condition, or disorder.

As used herein, the term "patient" refers to an animal who is suffering from hyperglycemia or diabetes or IGM. The preferred animal is a mammal, such as dogs, cats, horses, cows and humans. It is preferred that the patient is a human.

In this field the preferred patient population age is from 45 years onwards, most preferred from 60 years onwards.

The person skilled in the pertinent art is fully enabled to select a relevant test model and protocols to prove the beneficial effects of the invention.

Monitoring of glycemic status, as performed by patients and health care providers, is well known in the art such as reported in Diabetes Care "*Tests of Glycemia in Diabetes—American Diabetes Association*" 2003 26: S106-108 and described below. This publication is hereby incorporated by reference in their entirety.

The American Diabetes Association's technical review should be consulted for further information (e.g. Goldstein D E, Little R R, Lorenz R A, Malone J I, Nathan D, Peterson C M: Tests of glycemia in diabetes (Technical Review). *Diabetes Care* 18:896-909,1995).

Within only a few years, self-monitoring of blood glucose (SMBG) by patients has revolutionized management of diabetes. Using SMBG, patients with diabetes can work to achieve and maintain specific glycemic goals.

The subject of SMBG has been addressed extensively by two American Diabetes Association Consensus Conferences, which provide a comprehensive review of the subject (American Diabetes Association: Self-monitoring of blood glucose (Consensus Statement). *Diabetes Care* 17:81-86,1994—and—American Diabetes Association: Self-monitoring of blood glucose (Consensus Statement). *Diabetes Care* 10:93-99,1987) SMBG has supplanted urine glucose testing for most patients. Urine glucose testing by patients in the home setting consists of semiquantitative measurements based on single voidings or, less often, by more quantitative "blocks" collected over 4-24 h. The rationale is that urinary glucose values reflect mean blood glucose during the period of urine collection.

Blood and urine glucose testing and urine ketone testing provide useful information for day-to-day management of diabetes.

However, these tests cannot provide the patient and health care team with a quantitative and reliable measure of glycemia over an extended period of time. Measurements of glycated proteins, primarily hemoglobin and serum proteins, have added a new dimension to assessment of glycemia. With a single measurement, each of these tests can quantify average glycemia over weeks and months, thereby complementing day-to-day testing.

Glycated Hemoglobin (GHb) Testing:

GHb, also referred to as glycohemoglobin, glycosylated hemoglobin, $HbA_{1c}$, or $HbA_1$, is a term used to describe a series of stable minor hemoglobin components formed slowly and nonenzymatically from hemoglobin and glucose. The rate of formation of GHb is directly proportional to the ambient glucose concentration. Since erythrocytes are freely permeable to glucose, the level of GHb in a blood sample provides a glycemic history of the previous 120 days, the average erythrocyte life span. GHb most accurately reflects the previous 2-3 months of glycemic control.

Many different types of GHb assay methods are available to the routine clinical laboratory e.g. $HbA_{1c}$ can be measured by High Performance Liquid Chromatography (HPLC) using the ion-exchange method on a Bio-Rad Diamat analyzer. A back-up affinity method are used if hemoglobin variants or hemoglobin degradation peaks are observed.

Methods differ considerably with respect to the glycated components measured, interferences, and nondiabetic range. Glycated hemoglobin is often reported as hemoglobin $A_{1c}$. $HbA_{1c}$ has become the preferred standard for assessing glycemic control. In referring to this test, the term "A1C test" will be used.

A1C testing should be performed routinely in all patients with diabetes, first to document the degree of glycemic control at initial assessment, then as part of continuing care. Since the A1C test reflects a mean glycemia over the preceding 2-3 months, measurement approximately every 3 months is required to determine whether a patient's metabolic control has reached and been maintained within the target range.

The A1C test has been shown to predict the risk for the development of many of the chronic complications in diabetes, analogous to using cholesterol determinations to predict the risk for development of cardiovascular disease.

Glycated Serum Protein (GSP)

Because the turnover of human serum albumin is much shorter (half-life of 14-20 days) than that of hemoglobin (erythrocyte life span of 120 days), the degree of glycation of serum proteins (mostly albumin) provides an index of glycemia over a shorter period of time than does glycation of hemoglobin. Measurements of total GSP and glycated serum albumin (GSA) correlate well with one another and with measurements of glycated hemoglobin (A1C test). In situations where the A1C test cannot be measured or may not be useful (e.g., hemolytic anemias), the GSP assay may be of value in the assessment of the treatment regimen. Several methods have been described that quantify either total GSP or total GSA. One of the most widely used is called the fructosamine assay. Values for GSP vary with changes in the synthesis or clearance of serum proteins that can occur with acute systemic illness or with liver disease. In addition, there is continuing debate as to whether fructosamine assays should be corrected for serum protein or serum albumin concentrations.

A single measurement of GSP provides an index of glycemic status over the preceding 1-2 weeks, while a single A1C test provides an index of glycemic status over a considerably longer period of time, 2-3 months.

Measurement of GSP, regardless of the specific assay method, should not be considered equivalent to the A1C test, since it only indicates glycemic control over a short period of time. Therefore, GSP assays would have to be performed on a monthly basis to gather the same information as measured by the A1C test three to four times a year. Unlike the A1C test, GSP has not yet been shown to be related to the risk of the development or progression of chronic complications of diabetes.

The glucose level progression checks (e.g. GSP assay, A1C, insulin) are well known by the physicians and reported in the art e.g. by the American Diabetes Association.

The invention also relates to a treatment regimen, for the treatment of diabetes, e.g. type 2 diabetes wherein,
1. a patient treated by insulin and not adequately controlled by insulin alone is selected,
2. between 25 and 150 mg, preferably 50 mg or 100 mg of (S)-1-[(3-hydroxy-1-adamantyl)amino]acetyl-2-cyano-pyrrolidine, or a salt thereof, is to be administered in combination to insulin, daily, in said patient.

The invention also relates to a treatment regimen, for the treatment of diabetes, e.g. type 2 diabetes wherein,
1. a patient treated by at least one antidiabetic compound (e.g. one, two or three) and not adequately controlled by insulin alone is selected,
2. between 25 and 150 mg, preferably 50 mg or 100 mg of (S)-1-[(3-hydroxy-1-adamantyl)amino]acetyl-2-cyano-pyrrolidine, or a salt thereof, is to be administered in combination to insulin, daily, in said patient.

In the above described treatment regimen, the term "daily", applies to insulin and (S)-1-[(3-hydroxy-1-adamantyl)amino]acetyl-2-cyano-pyrrolidine (vildagliptin) or only to (S)-1-[(3-hydroxy-1-adamantyl)amino]acetyl-2-cyano-pyrrolidine (vildagliptin) e.g. when the patient contains within the body an insulin pump delivering the daily insulin dosage or any related device.

The invention also relates to a treatment regimen, for the treatment of diabetes, e.g. type 2 diabetes wherein,
1) a patient treated by insulin and showing hypoglycemic episodes preferably sever hypoglycemic events is selected,
2) between 25 and 150 mg, preferably 50 mg or 100 mg of (S)-1-[(3-hydroxy-1-adamantyl)amino]acetyl-2-cyano-pyrrolidine is to be administered in combination to insulin, daily, in said patient.

The invention also relates to a treatment regimen, for the treatment of diabetes, e.g. type 2 diabetes wherein,
1) a patient treated by at least one antidiabetic compound (e.g. one, two or three) and showing hypoglycemic episodes preferably sever hypoglycemic events is selected,
2) between 25 and 150 mg, preferably 50 mg or 100 mg of (S)-1-[(3-hydroxy-1-adamantyl)amino]acetyl-2-cyano-pyrrolidine is to be administered in combination to insulin, daily, in said patient.

The invention also relates to a treatment regimen, for the treatment of diabetes, e.g. type 2 diabetes wherein,
1) a patient treated by insulin and showing hypoglycemic episodes preferably sever hypoglycemic events is selected,
2) a DPP-4 inhibitor or a salt thereof, is to be administered in combination to insulin, daily, in said patient.

The invention also relates to a treatment regimen, for the treatment of diabetes, e.g. type 2 diabetes wherein,
i) a patient treated by at least one antidiabetic compound (one, two or three) and showing hypoglycemic episodes preferably sever hypoglycemic events is selected,
ii) a DPP-4 inhibitor or a salt thereof, is to be administered in combination to the at least one antidiabetic agent i), daily, in said patient.

The invention also relates to a treatment regimen, for the treatment of diabetes, e.g. type 2 diabetes wherein,
i) a patient treated by at least one antidiabetic compound and showing hypoglycemic episodes preferably sever hypoglycemic events is selected,
ii) a DPP-4 inhibitor or a salt thereof, is to be administered in combination to the at least one antidiabetic compound i), daily, in said patient.
iii) the dose or daily dose of at least one of the antidiabetic compound i) is progressively reduced until the desired glucose level is achieved.

The invention also relates to a treatment regimen, for the treatment of diabetes, e.g. type 2 diabetes wherein,
1) a patient treated by insulin and showing hypoglycemic episodes preferably sever hypoglycemic events is selected,
2) between 25 and 150 mg, preferably 50 mg or 100 mg of (S)-1-[(3-hydroxy-1-adamantyl)amino]acetyl-2-cyano-pyrrolidine or a salt thereof, is to be administered in combination to insulin, daily, in said patient.
3) the dose or the daily dose of insulin is progressively reduced until the desired glucose level is achieved i.e. blood glucose level e.g. via analysis of blood HbA1c level.

The invention also relates to a treatment regimen, for the treatment of diabetes, e.g. type 2 diabetes wherein,
i) a patient treated by at least one antidiabetic compound and showing hypoglycemic episodes preferably sever hypoglycemic events is selected,
ii) between 25 and 150 mg, preferably 50 mg or 100 mg of (S)-1-[(3-hydroxy-1-adamantyl)amino]acetyl-2-cyano-pyrrolidine or a salt thereof, is to be administered in combination to the at least one antidiabetic compound i), daily, in said patient.
iii) the dose or the daily dose of at least one antidiabetic compound i) is progressively reduced until the desired glucose level is achieved i.e. blood glucose level e.g. via analysis of blood HbA1c level.

Insulin, depending on it's delivery form, can be administered e.g. regularly over the day, twice a day, once a day, every 2 or 3 days.

The "at least one antidiabetic compound" according to the invention, can be administered e.g. regularly over the day, twice a day, once a day, every 2 or 3 days.

The invention also relates to a treatment regimen, for the treatment of diabetes, e.g. type 2 diabetes wherein,
1) a patient treated by insulin and showing hypoglycemic episodes preferably sever hypoglycemic events is selected,
2) between 25 and 150 mg, preferably 50 mg or 100 mg of (S)-1-[(3-hydroxy-1-adamantyl)amino]acetyl-2-cyano-pyrrolidine or a salt thereof, is to be administered in combination to a reduced dosage of insulin, daily, in said patient.

The invention also relates to a treatment regimen, for the treatment of diabetes, e.g. type 2 diabetes wherein,
i) a patient treated by at least one antidiabetic compound and showing hypoglycemic events preferably sever hypoglycemic events is selected,
ii) a DPP-4 inhibitor or a salt thereof, is to be administered in combination to a reduced dosage of at least one of the antidiabetic compound i), daily, in said patient.

The invention also relates to a treatment regimen, for the treatment of diabetes, e.g. type 2 diabetes wherein,
i) a patient treated by at least one antidiabetic compound (e.g. one, two or three) and showing hypoglycemic episodes preferably sever hypoglycemic events is selected,
ii) between 25 and 150 mg, preferably 50 mg or 100 mg of (S)-1-[(3-hydroxy-1-adamantyl)amino]acetyl-2-cyano-pyrrolidine or a salt thereof, is to be administered in combination to a reduced dosage of at least one antidiabetic compound of i), daily, in said patient.

A treatment regimen as described herein, wherein (S)-1-[(3-hydroxy-1-adamantyl)amino]acetyl-2-cyano-pyrrolidine is replaced by any other DPP-4 inhibitor especially the ones described herein, and the dosage is adapted to the selected specific DPP-4 inhibitor.

A treatment regimen, method or use as described herein wherein between 25 mg and 200 mg of DPP-4 inhibitor or a salt thereof is administered daily to the treated patient. The preferred daily administration of sitagliptin is between 25 and 100 mg.

A treatment regimen, method or use as described herein wherein the DPP-4 inhibitor can be administered in combination with a further antidiabetic compound such as metformin, a glitazone (e.g. pioglitazone or rosiglitazone) or a sulfonylurea.

A treatment regimen, method or use as described herein, wherein the treated patient is suffering from insulin-dependent diabetes mellitus (IDDM), non-insulin-dependent diabetes mellitus (NIDDM) or type A insulin resistance.

A treatment regimen, method or use as described herein wherein the DPP-4 inhibitor can be administered in combination with insulin and or a further antidiabetic compound such as with one, two or three antidiabetic compounds selected from metformin, nateglinide, glitazones (preferably pioglitazone or rosiglitazone), sulfonylureas, GLP-1 or GLP-1 analogues (preferably exendin-4), a cannabinoid receptor-1 (CB1) antagonists (preferably rimonaban) and insulin. When the patient is treated with two antidiabetic compounds, the combination can be; metformin+a sulfonylureas, metformin+a glitazone, metformin+a GLP-1 analogue, metformin+a CB1 antagonist, a glitazone+a sulfonylurea, metformin+insulin, a glitazone+insulin, a GLP-1 analogue+a sulfonylurea, a sulfonylurea+insulin.

Preferably the treated patient in the above described methods or uses, is suffering from hyperglycemia and hypoglycemic events e.g. sever hypoglycemic events after insulin administration. Most preferably the patient suffering from hyperglycemia, is suffering from a disease selected from diabetes mellitus, type I or insulin-dependent diabetes mellitus (IDDM), type II or non-insulin-dependent diabetes mellitus (NIDDM), type A insulin resistance, IGM, IFG or IGT. In a preferred embodiment the patient is suffering from type II diabetes or IGT. In another preferred embodiment the treated patient is a patient whose disease e.g. hyperglycemia or glucose level, was not adequately controlled by insulin alone. In another preferred embodiment the treated patient is a patient whose disease e.g. hyperglycemia or glucose level, was not adequately controlled by at least one antidiabetic compound.

The term "at least one antidiabetic compound" according to the present invention does not cover DPP-4 inhibitors.

The structure of the active agents identified by code nos., generic or trade names may be taken from the actual edition of the standard compendium "The Merck Index" or from databases, e.g. Patents International (e.g. IMS World Publications). The corresponding content thereof is hereby incorporated by reference. Any person skilled in the art is fully enabled to identify the active agents and, based on these references, likewise enabled to manufacture and test the pharmaceutical indications and properties in standard test models, both in vitro and in vivo.

The herein described pharmaceutical preparations are for enteral, such as oral, and also rectal or parenteral, administration to homeotherms, with the preparations comprising the pharmacological active compound either alone or together with customary pharmaceutical auxiliary substances. For example, the pharmaceutical preparations consist of from about 0.1% to 90%, preferably of from about 1% to about 80%, of the active compound. Pharmaceutical preparations for enteral or parenteral, and also for ocular, administration are, for example, in unit dose forms, such as coated tablets, tablets, capsules or suppositories and also ampoules. These are prepared in a manner that is known per se, for example using conventional mixing, granulation, coating, solubulizing or lyophilising processes. Thus, pharmaceutical preparations for oral use can be obtained by combining the active compound with solid excipients, if desired granulating a mixture which has been obtained, and, if required or necessary, processing the mixture or granulate into tablets or coated tablet cores after having added suitable auxiliary substances.

The dosage of the active compound can depend on a variety of factors, such as mode of administration, homeothermic species, age and/or individual condition.

Preferred dosages, for those active ingredients of the pharmaceutical combination according to the present invention that are commercially available, are especially therapeutically effective commercially available dosages.

The dosage of the active compound can depend on a variety of factors, such as mode of administration, homeothermic species, age and/or individual condition.

The corresponding active ingredient or a pharmaceutically acceptable salt thereof may also be used in form of a hydrate or include other solvents used for crystallization.

The exact dosage will of course vary depending upon the compound employed, mode of administration and treatment desired. The compound may be administered by any conventional route, non-oral or preferably orally.

In general, satisfactory results are obtained when DPP-IV inhibitor especially LAF237 is administered at a daily dosage of from about 0.01 to 50 mg/kg, more preferred doses ranged from 0.1 to 50 mg/kg.

Treatment with insulin or with at least one antidiabetic compounds is well described in the art.

For the larger mammals, an indicated total daily dosage is in the range from about 0.01 to 100 mg/kg of the compound, conveniently administered in divided doses 2 to 4 times a day in unit dosage form containing for example from about 0.1 to about 50 mg of the compound in sustained release form.

Preferably for the DPP-IV inhibitor especially LAF237 an indicated total daily dosage is in the range from between 1 and 500 mg, preferably between 10 and 200 mg of active ingredient.

Another preferred DPP-IV inhibitor especially LAF237 daily oral dosage is between 1 and 100 mg preferably between 10 and 100 mg e.g. 10 mg, most preferably between 25 and 100 mg e.g. 25 mg or 30 or 40 or 50, 61, 70, 90, 100, 150 mg. The very preferred daily oral dosage of LAF237 is between 50 and 100 mg.

Appropriate unit doses for oral administration contain for example about 25 to about 200, or about 25 to about 100 mg of DPP-IV inhibitor especially LAF237, such as preferably 25, 50 or 100 mg. Appropriate doses for parenteral administration contain for example about 1 to about 100 mg of the compound, e.g. from 10 to 50 mg.

The DPP-IV inhibitor can also be administered every day or only every two days, or twice a week.

The compounds may be administered in similar manner to known standards for uses in these utilities. The suitable daily dosage for a particular compound will depend on a number of factors such as its relative potency of activity. A person skilled in the pertinent art is fully enabled to determine the therapeutically effective dosage.

The compound of the invention may be administered in free base for or as a pharmaceutically acceptable acid addition or quaternary ammonium salt. Such salts may be prepared in conventional manner and exhibit the same order of activity as the free forms. If these compounds have, for example, at least one basic center, they can form acid addition salts. Corresponding acid addition salts can also be formed having, if desired, an additionally present basic center. The compounds having an acid group (for example COOH) can also form salts with bases. For example, the compounds to be combined can be present as a sodium salt, as a maleate or as a dihydrochloride. The active ingredient or a pharmaceutically acceptable salt thereof may also be used in form of a hydrate or include other solvents used for crystallization.

A combined preparation which comprises a DPP-IV inhibitor in free or pharmaceutically acceptable salt form and insulin or at least one antidiabetic compound (one, two or three) and optionally at least one, i.e., one or more, e.g. two, pharmaceutically acceptable carrier for simultaneous, separate or sequential use is especially a "kit of parts" in the sense that the components, a DPP-IV inhibitor in free or pharmaceutically acceptable salt form and insulin or the at least one antidiabetic compound, can be dosed independently or by use of different formulations with distinguished amounts of the components, i.e. at different time points or simultaneously. The parts of the kit of parts can then, e.g., be administered simultaneously or chronologically staggered, that is at different time points and with equal or different time intervals for any part of the kit of parts. Preferably, the time intervals are chosen such that the effect on the treated disease or condition in the combined use of the parts is larger than the effect which would be obtained by use of only any one of the components.

A therapeutically effective amount of each of the components of the combination of the present invention may be administered simultaneously or sequentially and in any order, and the components may be administered separately or as a fixed combination.

The pharmaceutical compositions according to the invention can be prepared in a manner known per se and are those suitable for enteral, such as oral or rectal, and parenteral administration to mammals (warm-blooded animals), including man, comprising a therapeutically effective amount of the pharmacologically active compound, alone or in combination with one or more pharmaceutically acceptable carries, especially suitable for enteral or parenteral application.

To further illustrate the invention, but not by way of limitation, the following clinical study is provided.

The invention has been described above by reference to preferred embodiments but, as those skilled in the art will appreciate, many additions, omissions and modifications are possible all within the scope of the claims below.

All patents and literature references cited in this specification are hereby incorporated by reference in their entirety. In case of inconsistencies, the present description, including the definitions and interpretations, will prevail.

EXAMPLE 1

Clinical Study

Insulin is used as a representative of antidiabetic compounds inducing hypoglycemic events. Equivalent studies can be run with other antidiabetic compounds (e.g. one, two or three) to show the claimed unexpected advantage of DPP-4 inhibitors.

Protocol Synopsis

Title of Study:

A multicenter, double-blind, randomized, parallel-group study to compare the effect of 24 weeks treatment with LAF237 50 mg bid to placebo as add-on therapy in patients with type 2 diabetes treated with insulin.

Study Purpose:

The present study is designed to demonstrate the efficacy and safety of add-on therapy with LAF237 50 mg bid in patients with type 2 diabetes treated with insulin. This study support the global regulatory approval of LAF237 as combination therapy with insulin in the treatment of type 2 diabetes.

Objectives:

Primary objective: To demonstrate the efficacy of add-on therapy with LAF237 in patients with type 2 diabetes treated with insulin by testing the hypothesis that the HbA1c reduction with LAF237 50 mg bid is superior to that with placebo after 24 weeks of treatment.

Secondary: Critical Variables 1—To demonstrate the efficacy of add-on therapy with LAF237 in patients with type 2 diabetes treated with insulin by testing the hypothesis that the fasting plasma glucose (FPG) reduction with LAF237 50 mg bid is superior to that with placebo after 24 weeks of treatment.

2—To demonstrate the safety of LAF237 in patients with type 2 diabetes treated with insulin by showing that add-on therapy with LAF237 50 mg bid has a similar adverse event profile compared to placebo after 24 weeks of treatment.

3—To demonstrate the efficacy of add-on therapy with LAF237 in patients with type 2 diabetes treated with insulin by showing that the mean reduction of daily insulin dosage and mean reduction in number of daily insulin injections in combination with LAF237 50 mg bid are greater than those with placebo after 24 weeks of treatment.

4—To demonstrate the efficacy of add-on therapy with LAF237 in patients with type 2 diabetes treated with insulin by showing that the responder rates with LAF237 50 mg bid are greater than those with placebo after 24 weeks of treatment.

5—To demonstrate the efficacy of add-on therapy with LAF237 in patients with type 2 diabetes treated with insulin across baseline HbA1c subgroups to assess whether or not the therapeutic efficacy of LAF237 (lowering of HbA1c with 50 mg bid vs. placebo) is greater in patients with high baseline HbA1c (>9%) than patients with lower baseline HbA1c (<9%) after 24 weeks of treatment.

Exploratory Variables

1—To explore the mechanism of action of LAF237 in add-on therapy in patients with type 2 diabetes treated with insulin by testing the hypotheses that LAF237 50 mg bid improves beta-cell function (indexed by the fasting proinsulin concentration, fasting proinsulin/insulin ratio and HOMA B) and reduces insulin resistance (indexed by the fasting insulin concentration and HOMA IR) relative to placebo after 24 weeks of treatment.

2—To explore the ancillary clinical benefits of add-on therapy with LAF237 in patients with type 2 diabetes treated with insulin by testing the hypotheses that LAF237 50 mg bid has a beneficial effect on fasting plasma lipid profiles and is body weight-neutral relative to placebo after 24 weeks of treatment.

3—To explore the ancillary benefits of add-on therapy with LAF237 in patients with type 2 diabetes treated with insulin by showing that LAF237 50 mg bid has a favorable impact on quality of life, patient satisfaction, and work productivity relative to placebo after 24 weeks of treatment.

Population:

Patients with type 2 diabetes who are inadequately controlled on insulin can benefit from intensification of their insulin regimen or by the addition of an oral antidiabetic agent. In this study, 30 Units of insulin per day for a minimum of 4 weeks prior to visit 1, will be eligible to participate in this study.

The population will consist of male and female patients (non-fertile or of childbearing potential using a medically approved birth control method) aged 18 to 80 years, with an HbA1c of 7.5-11%.

This is an outpatient multicenter study which will be conducted in approximately 80 centers in the US and Europe. Approximately 384 patients will be screened in order to randomize 192 patients.

Inclusion/Exclusion Criteria:

Inclusion criteria: male or female (non-fertile or of childbearing potential using a medically approved birth control method) patients with type 2 diabetes, previously treated with insulin for at least 3 months, aged 18-80 years, body mass index of 22-45 kg/m2, HbA1c 7.5-11% inclusive, FPG_270 mg/dL (15 mmol/L) and agreement to maintain prior diet and exercise.

Exclusion criteria: pregnant or lactating female; a history of type 1 diabetes, diabetes that is a result of pancreatic injury or secondary forms of diabetes, acute metabolic diabetic complications within past 6 months; evidence of significant diabetic complications; acute infections which may affect blood glucose control within the past 4 weeks; Torsades de Pointes, ventricular tachycardia, ventricular fibrillation; percutaneous coronary intervention in the past 3 months; myocardial infarction, coronary artery bypass surgery, or unstable angina within the past 6 months; congestive heart failure NYHA class III or IV; second degree AV block (Mobitz 1 and 2), third degree AV block, prolonged QTc; malignancy including leukemia and lymphoma within the last 5 years; liver disease; acromegaly or treatment with growth hormone; treatment with any oral antidiabetic medication within the last 3 months; treatment with an insulin pump; chronic oral or parenteral corticosteroid treatment within the past 8 weeks; treatment with class Ia, Ib, Ic, or III anti-arrhythmics; significant laboratory abnormalities.

Investigational and Reference Therapy:

In addition to treatment with insulin, patients are assigned to double-blind treatment of LAF237 50 mg bid or placebo in a ratio of 1:1.

Study Design:

This is a multicenter, randomized, double-blind, placebo-controlled study. Patients with type 2 diabetes (HbA1c 7.5-11%) who have been treated for at least 3 months with insulin is eligible for participation in the trial. Eligible patients are randomized equally to LAF237 50 mg bid or placebo in addition to continuing their insulin therapy. The insulin dose can be adjusted downward as clinically indicated but upward adjustments should not exceed 25% of the baseline insulin dose.

Each patient attends one screening visit (Week-4) where the inclusion/exclusion criteria is assessed. Eligible patients are then be randomized at Visit 2 (Baseline, Day 1) and complete 5 further visits over a period of 24 weeks of treatment with LAF237 or placebo added to insulin.

Efficacy Assessments:

Primary efficacy assessments: HbA1c; Secondary efficacy assessments: Fasting plasma glucose, fasting lipids (triglycerides, total cholesterol, calculated LDL, HDL, calculated non-HDL, calculated VLDL), body weight, beta-cell function (fasting proinsulin, fasting proinsulin/insulin ratio, HOMA B), insulin resistance (fasting insulin, HOMA IR), mean daily insulin dose, mean daily number of insulin injections, and responder rates.

patients with type 2 diabetes who have been treated with insulin for at least 3 months, and at least.

Other Assessments:

Safety assessments include the monitoring of adverse events, vital signs, physical examinations laboratory evaluations (hematology, biochemistry and urinalysis), and electrocardiograms. Other assessments include quality of life questionnaires.

Data Analysis:

The hypothesis for testing superiority of LAF237 50 mg bid to placebo, both LAF237 and placebo combined with insulin, for the effect of reducing HbA1c will be $H_0: \delta_{LAF\ 50\ mg\ bid} = \delta_{Placebo}$ versus Ha: $\epsilon_{LAF50\ mg\ bid}$ different from $\delta_{Placebo}$ where $\delta$ is the mean change from baseline in the treatment group indicated by the subscript. An analysis of covariance (ANCOVA) model are fitted including terms for treatment, baseline HbA1c and region. The least squares mean ("adjusted mean") change from baseline for each treatment group, the difference in the least squares mean changes between the two treatment groups (LAF237 50 mg bid—placebo), and the two-sided 95% confidence interval for the difference along with the p value for the treatment comparison are obtained from the primary analysis model and presented. Secondary efficacy variables are assessed using a similar model.

Patients were instructed to perform self-monitored blood glucose measurements (SMBG) any time hypoglycemia was suspected and prior to breakfast at least 3 times per week. Hypoglycemia was defined as symptoms suggestive of low blood glucose confirmed by SMBG<3.1 mmol/L plasma glucose equivalent. Severe hypoglycemia was defined as any episode requiring the assistance of another party (with low plasma glucose value<3.1 mmol/L unless the severity of the event precluded glucose determination).

Therefore according to the present invention, the term "Severe hypoglycemia" is preferably defined as an episode of low plasma glucose value<3.8 mmol/L, preferably<3.1 mmol/L.

All laboratory assessments were made by central laboratories. $HbA_{1c}$ was quantified with HPLC methodology referring to a DCCT standard at a National Glycohemoglobin Standardization Program (NGSP) level 1 certified laboratory (Bioanalytical Research Corporation [BARC]-EU, Ghent, Belgium or Covance-US, Indianapolis, Ind.) or at an NGSP network laboratory (Diabetes Diagnostic Laboratory, Columbia, Mo.). All other laboratory assessments were made by BARC-US (Lake Success, N.Y.) or BARC-EU. Assays were performed according to standardized and validated procedures according to good laboratory practice.

Results:

Data confirms that LAF237 is associated with fewer severe hypoglycaemic episodes when added to insulin. Patients treated only with insulin show a significantly higher number of hypoglycaemic episodes especially severe hypoglycaemic episodes (1). Patients treated with insulin and LAF237 did not show any severe hypoglycaemic episodes (1).

(1) Grade 2 hypoglycemic events: Blood glucose<3.1 and symptoms suggestive of hypoglycemia.

Vildagliptin (LAF237) appear to have a protective effect against insulin-induced hypoglycemia.

Table 1 displays the number of patients experiencing one or more episodes (panel A), the total number of episodes (panel B) and the number of severe hypoglycemic episodes (panel C) in patients randomized to vildagliptin 50 mg bid or placebo added to insulin. In the vildagliptin group, 33 patients reported a total of 113 events, none of which were severe, ie, requiring assistance of another party. In the placebo group, 45 patients reported a total of 185 events, 6 of which were severe. Both the number hypoglycemic events and the number of severe events were statistically significantly lower in the vildagliptin group (P<0.001 and P=0.032 respectively, based on chi-square test of two Poisson rates).

TABLE 1

Number of patients reporting any hypoglycemic episode (Panel A), total number of hypoglycemic episodes reported (Panel B) and number of severe hypoglycemic episodes (Panel C) during 24-week treatment with vildagliptin 50 mg bid (n = 144) or placebo (n =152).

| Panel | Vildagliptin + Insulin Nb. of Patients | Placebo + Insulin Nb. of Patients |
|---|---|---|
| A | 33 | 45 |
| B | 113 | 185 |
| C | 0 | 6 |

*P < 005),
***P < 0.001 vs placebo.

In addition, the dosage of insulin can be reduced in patient is treated by LAF237.

What is claimed is:

1. A method for reducing hypoglycemic events or severe hypoglycemic events in a patient suffering from hyperglycemia, diabetes mellitus, insulin-dependent diabetes mellitus (IDDM), non-insulin-dependent diabetes mellitus (NIDDM), type A insulin resistance, Impaired Glucose Metabolism (IGM), Impaired Fasting Glucose (IFG) or Impaired Glucose Tolerance (IGT), said method comprising:
   i) selecting a patient treated by insulin and showing hypoglycemic episodes or severe hypoglycemic events; and
   ii) administering vildagliptin or a salt thereof, in combination with insulin to said patient.

2. The method according to claim 1, wherein the vildagliptin and insulin are administered simultaneously or sequentially, and in any order.

3. The method of claim 1 wherein the vildagliptin is administered in amounts of between 25 and 150 mg per day.

4. The method according to claim 1 wherein the patient is under treatment with an additional one, two or three antidiabetic compounds.

5. The method of claim 4, wherein the additional antidiabetic compound is selected from metformin, nateglinide, glitazones, sulfonylureas, GLP-1 or GLP-1 analogues, and cannabinoid receptor-1 (CB1) antagonists.

6. The method of claim 4, wherein the patient is under treatment with an additional two antidiabetic compounds selected from: metformin and a sulfonylurea, metformin and a glitazone, metformin and a GLP-1 analogue, metformin and a CB1 antagonist, a glitazone and a sulfonylurea, and a GLP-1 analogue and a sulfonylurea.

7. The method of claim 1 wherein the hypoglycemic events or severe hypoglycemic events are resulting from insulin treatment or from treatment with insulin and at least one additional antidiabetic compound.

8. The method according to claim 1 wherein between 25 and 200 mg of vildagliptin or a salt thereof, is administered daily.

9. The method of claim 5, wherein the glitazone is pioglitazone or rosiglitazone.

10. The method of claim 5, wherein the GLP-1 analogue is exendin-4.

* * * * *